United States Patent [19]

Gumprecht et al.

[11] Patent Number: 5,663,478
[45] Date of Patent: Sep. 2, 1997

[54] RECOVERY OF ALUMINUM AND/OR FLUORIDE VALUES FROM USED ALUMINUM CHLOROFLUORIDES

[75] Inventors: William Henry Gumprecht, Wilmington, Del.; William Joel Huebner, Elkton, Md.

[73] Assignee: E.I. Du Pont de Nemours and Company, Wilmington, Del.

[21] Appl. No.: 600,121

[22] Filed: Feb. 12, 1996

Related U.S. Application Data

[63] Continuation of Ser. No. 279,383, Jul. 25, 1994, abandoned, which is a continuation-in-part of Ser. No. 114,643, Sep. 3, 1993, abandoned.

[51] Int. Cl.$^6$ ............................................. C01F 7/48
[52] U.S. Cl. .................. 588/248; 423/111; 423/116; 423/122; 423/465; 23/305 A
[58] Field of Search .................... 423/111, 116, 423/122, 127, 495, 465; 588/206, 248; 502/24, 514, 231; 23/305 A

[56] References Cited

U.S. PATENT DOCUMENTS

| 2,783,128 | 2/1957 | Wendt | 23/88 |
|---|---|---|---|
| 2,991,159 | 7/1961 | Wendt | 23/88 |
| 3,231,514 | 1/1966 | Sechrist et al. | 502/24 |
| 3,427,254 | 2/1969 | Muller et al. | 502/231 |
| 4,508,689 | 4/1985 | Bush et al. | 423/127 |
| 4,597,956 | 7/1986 | Hinchey et al. | 423/328 |
| 4,816,122 | 3/1989 | Lever | 204/182.4 |
| 4,925,993 | 5/1990 | Zawalski | 570/151 |
| 5,057,470 | 10/1991 | Kellner | 502/35 |

FOREIGN PATENT DOCUMENTS

| 5-140011 | 6/1993 | Japan. | |
| 899473 | 1/1982 | U.S.S.R. | 423/116 |

OTHER PUBLICATIONS

Article "Dimorphism in Aluminum Fluoride Trihydrate" [abstracted from a thesis submitted by Francis J. Frere to the Graduate School of New York Univ.] by W. F. Ehret and F. J. Frere [Contribution from the Chemical Laboratories of New York University] vol. 67 pp. 64–68 Journal of the American Chemical Society (Jan. 1945).

Primary Examiner—Gary P. Straub
Assistant Examiner—Timothy C. Vanoy
Attorney, Agent, or Firm—James E. Shipley

[57] ABSTRACT

A process is disclosed for treating used aluminum chlorofluoride catalyst either alone or mixed with organics. It involves forming a solution of the catalyst in water or an aqueous acid and then adjusting the pH and/or composition of the aqueous phase formed to precipitate compounds containing the aluminum and/or fluorine.

10 Claims, No Drawings

RECOVERY OF ALUMINUM AND/OR FLUORIDE VALUES FROM USED ALUMINUM CHLOROFLUORIDES

CROSS REFERENCE TO RELATED APPLICATION

This is a continuation of application Ser. No. 08-279,383 filed 25 Jul. 1994 which is now abandoned, which is a continuation-in-part of application Ser. No. 08-114,643 filed 03 Sep. 1993 which is now abandoned.

BACKGROUND OF THE INVENTION

This invention relates to the field of disposal of used aluminum chlorofluorides and the recovery of the aluminum and/or fluoride values contained in them. Anhydrous aluminum chloride ($AlCl_3$) is used to prepare (an isomerization catalyst in reactions to produce various halocarbons including 1,1-difluorotetrachloroethane (CFC-112a), 1,1,1-trifluorotrichloroethane (CFC-113a) and 1,1-dichlorotetrafluoroethane (CFC-114a). With prolonged contact with such chlorofluorocarbons during the isomerization reactions, the catalyst approaches aluminum trifluoride in composition, but always retains some mount of chloride. Depending upon the particular reaction conditions, reactant and the amount of reactant isomerized per weight of catalyst, the chloride content will vary. Therefore, the used catalyst is usually designated as simply "aluminum chlorofluoride."

When the used catalyst is removed from the process, it is normally in combination with residual organics and/or water-immiscible solvents. The used catalyst is hazardous. Disposal of the used catalyst is usually difficult, and the aluminum and fluoride values are wasted. In the past, the catalyst has been disposed of by conventional methods, such as incineration, neutralization, and landfilling. These disposal methods are not cost effective and involve the shipping and handling of toxic wastes.

Objects of the instant invention are to recover the aluminum and/or fluoride values contained in used aluminum chlorofluoride catalyst, to recover the organics which are mixed with the used aluminum chlorofluoride catalyst and to recover the indicated values without having to concentrate the organics in the used aluminum chlorofluoride catalyst. Another object is to convert a hazardous material into a less hazardous material to allow for easier and safer disposal.

SUMMARY OF THE INVENTION

A process has been discovered for treating used aluminum chlorofluoride catalyst comprising mixing the used aluminum chlorofluoride catalyst with water or an aqueous add to form an aqueous solution, adjusting the pH of the aqueous solution to precipitate the aluminum and/or fluoride values contained in the aqueous solution, and separating the precipitated aluminum and/or fluoride values from the aqueous solution.

A process has been discovered for treating a mixture of used aluminum chlorofluoride catalyst and organics comprising mixing the organics and used aluminum chlorofluoride catalyst with water or an aqueous add to form an organic phase and an aqueous phase, separating the organic phase from the aqueous phase, adjusting the pH of the aqueous phase to precipitate the aluminum and/or fluoride values contained in the aqueous phase, and separating the precipitated aluminum and/or fluoride values from the aqueous phase.

A process for producing cryolite from used aluminum chlorofluoride catalyst comprising:

mixing the used aluminum chlorofluoride catalyst with water or an aqueous add to form an aqueous solution, contacting the aqueous solution with a stoichiometric mount of sodium fluoride to cause cryolite to precipitate, and separating the precipitated cryolite from the aqueous solution.

DESCRIPTION OF THE PREFERRED EMBODIMENTS

In the present invention the used aluminum chlorofluoride catalyst is normally present as a mixture of solids with organic chlorofluorocarbons. Usually, this mixture is in slurry form. The amount of used aluminum chlorofluoride catalyst in this mixture varies. The used catalyst of this invention is aluminum chlorofluoride which has been used in the isomerization of various halocarbons, including 1,2-difluorotetrachloroethane (CFC-112); 1,1,2-trifluorotrichloroethane (CFC-113) and 1,2-dichlorotetrafluoroethane (CFC-114). However, it is also possible to use this invention with other aluminum chlorofluoride catalysts, such as the catalyst which has been used in the synthesis of perfluoro-n-pentene-2, a precursor for 2,3-dihydroperfluoro-n-pentane (HFC-43-10mee).

Aluminum trifluoride is nearly insoluble in water, (0.559 grams/100 milliliters at 25° C.). Therefore, it is surprising that, when the used aluminum chlorofluoride catalyst, either in the presence or absence of organics, is added to water, the used catalyst readily dissolves to form an aqueous solution even though there is a large amount of fluoride present.

When a mixture of organics and used aluminum chlorofluoride catalyst is mixed with water or an aqueous add, dissolution and phase separation occurs. Normally, two distinct phases will readily form. Thereafter, the aqueous phase is separated from the organic phase. This separation can be accomplished by any method known in the art, e.g., bottom withdrawal, decantation, etc.

Although pressure is not critical, when operating the invention with aluminum chlorofluoride which has been used to isomerize volatile reactants, such as CFC-114, it may be necessary to carry out the process in a closed system under super-atmospheric pressure because of the subambient boiling point of the crude products, such as CFC-114a, which have been produced.

The separated organic phase may be returned to the main process or used in other ways for recovery of useful products.

The aqueous phase is very acidic, with a pH normally less than about 3. The pH can be adjusted by any method which causes the aluminum and fluoride values to precipitate. This is normally done by adding an aqueous alkali, such as sodium hydroxide, potassium hydroxide, ammonium hydroxide, calcium hydroxide or other aqueous bases such as carbonates and bicarbonates. A preferred alkali is aqueous sodium hydroxide (NaOH). Another method is the addition of a soluble cation, such as calcium ion, with contemporaneous or subsequent addition of alkali to facilitate the precipitation of a fluoride, for example, calcium fluoride.

To illustrate, above a pH of about 3.5, precipitation from the aqueous phase of a mixture of trisodium hexafluoroaluminate ("cryolite") and hydrated aluminum hydroxyfluorides can occur when using NaOH. The aqueous phase containing the precipitate becomes buffered between a pH of about 4 to 5 as continued precipitation occurs with the further addition of NaOH. When the pH reaches about 8, precipitation is usually complete, leaving only trace amounts of dissolved aluminum and fluoride in solution, e.g., usually less than 0.04% of aluminum and fluoride in the aqueous phase.

The precipitate which is formed from the aqueous phase, e.g., "cryolite" and aluminum hydroxyfluorides, may be separated from the solution by any convenient method, such as filtration, decantation or centrifugation. The separated precipitate may then be used for other useful purposes or drummed and landfilled. Chlorides which remain in solution can be easily used as aqueous NaCl or treated as aqueous waste.

Another embodiment of the instant invention is the addition of a stoichiometric amount of sodium fluoride to the aqueous phase formed by the addition of water to used aluminum chlorofluoride catalyst. This addition can be accomplished by any known method and does not require the adjustment of pH. Specifically, a stoichiometric amount of sodium fluoride, preferably as an aqueous solution, is added to the aqueous phase of used aluminum chlorofluoride catalyst. Thereafter, cryolite is formed and is allowed to precipitate. The cryolite can then be separated from the aqueous solution by any known method including settling. It is possible to recover high percentages of aluminum and fluoride values as cryolite using this embodiment.

EXAMPLES

Example 1

1. A slurry of 2430 grams of used aluminum chlorofluoride catalyst (11.61 wt. % solids) in crude 1,1,1-trichlorotrifluoroethane (CFC-113a) was added rapidly with stirring to 2430 milliliters of deionized water in a 5 liter flask having an addition funnel, agitator, thermometer and reflux condenser. The temperature of the mixture increased from ambient to 36° C. with gentle reflux of the organics. Two layers formed with a very small amount of amorphous solids at the interface. The clear, nearly colorless upper aqueous layer was separated and analyzed. Its pH was 1.86. It contained 0.259 wt. % chloride, 5.36 wt. % fluoride and 2.57 wt. % aluminum which corresponds to a used catalyst composition of $AlF_{2.96}Cl_{0.08}$. If allowed to stand, highly crystalline aluminum trifluoride trihydrate will separate from this solution and cause the solution to change in composition. Even though this occurs, it is not a quantitative method of recovering the aluminum and fluoride values.

Prior to the precipitation of the aluminum trifluoride trihydrate, sufficient aqueous 10% sodium hydroxide solution (175 grams) was added to a 535 gram portion of this solution with stirring at ambient temperature to bring the pH to 6.99. Precipitation occurred in a buffered zone between pH 4.5–5.0. A sample of the clear supernatant from a settled portion of this suspension contained 0.214 wt. % chloride, 0.033 wt. % fluoride and 0.02 wt. % aluminum. A portion of the precipitate was collected by filtration, washed thoroughly with deionized water and dried in an oven. X-ray fluorescence (XRF) found the dried solid to contain sodium and aluminum as the major metals present. X-ray diffraction (XRD) found the major crystalline phase in the solid to be trisodium hexafluoroaluminate ($Na_3AlF_6$, "cryolite"). A minor-to-major crystalline phase of $Al(OH,F)_3$ hydrate was also present. The stoichiometry which most nearly describes the formation of these products is:

$$3AlF_2Cl+6NaOH \rightarrow Na_3AlF_6+2Al(OH)_3+3NaCl$$

The presence of $Al(OH,F)_3$ suggests that hydrolysis of the Al—F bond was incomplete.

Example 2

A used catalyst slurry (10.43 wt. % solids) that had been used to isomerize 135 batches of 1,1,2-trifluorotrichloroethane (CFC-113) to crude CFC-113a was used for this experiment. This used catalyst had an approximate composition of $AlF_{2.97}Cl_{0.40}$. A 1435 gram portion of the slurry was hydrolyzed in 1435 milliliters of deionized water in the same manner as Example 1. Crystals of aluminum trifluoride trihydrate were allowed to separate from the aqueous layer over several days. A 553 gram portion of the clear supernatant (pH 1.40, 5.07 wt. % fluoride, 1.05 wt. % chloride) above these crystals was treated with enough 18% sodium hydroxide (101 grams) to bring the pH to 6.88. The precipitate that separated, after filtration, washing and drying, was shown by XRD to consist of a minor-to-major amount of "cryolite" and a very small amount of $AlF_{1.65}(OH)_{1.35}$ hydrate in the crystalline phases present in the precipitate. Again, hydrolysis of the Al—F bond was incomplete.

Example 3

An aqueous solution of used catalyst was generated from 1450 grams of a slurry containing about 10 wt. % solids and 1450 milliliters of deionized water as previously described in Example 1. The solution contained 4.52 wt. % fluoride and 0.89 wt. % chloride. A 500 gram portion of this solution was adjusted from a pH of 2.16 to 6.84 using 270 grams of 10% aqueous potassium hydroxide. The clear supernatant, after settling of the solids, contained 98 ppm fluoride and 0.73 wt. % chloride. The collected, washed and dried solids had, by XRD, major crystalline phases of dipotassium pentafluoroaluminate monohydrate ($K_2AlF_5$ hydrate) and aluminum oxyhydroxide [AlO(OH),"boehimite"] and a minor crystalline phase of dialuminumtrifluorotrihydroxide $[Al_2F_3(OH)_3]$.

Example 4

The used catalyst in this Experiment had been used for 225 hours at 60° C. to isomerize a mixture of CFC-113 and 1,2-difluorotetrachloroethane (CFC-112) to crude CFC-113a and 1,1-difluorotetrachloroethane (CFC-112a), producing 2500 kilograms of CFC-112a per kilogram of catalyst. A 1728 gram portion of this used catalyst slurry (3.15 wt. % solids) was added to 1725 milliliters of deionized water. The temperature increased 3° C. above ambient. The aqueous layer had a pH of 2.6. The fluoride content was 1.35 wt. %, and the chloride content was 0.097 wt. %. With a measured aluminum content of 0.65 wt. % in the aqueous layer, the approximate composition of the used catalyst was $AlF_{2.95}Cl_{0.11}$.

About 600 milliliters of the aqueous layer was brought to a pH of 7.0 with 18% sodium hydroxide. The clear supernatant above the precipitated solids contained 0.020 wt. % fluoride and 36 ppm aluminum. The filtered, washed and dried precipitate had, as the major crystalline phase, $Al_2F_{3.24}(OH)_{2.76}$ monohydrate. "Cryolite" was a minor-to-major crystalline phase.

Example 5

Using the same used catalyst slurry as described in Example 3, 1230 grams was added to 1230 milliliters of deionized water. The aqueous layer was separated, and 225 grams of it was adjusted to a pH of 7.11 using 37.1 grams of 18% sodium hydroxide. The suspension was stirred, heated to 90°–94° C. and maintained for one hour. It was then stirred and allowed to cool to 50° C. before being cooled further to 25° C. using externally applied cooling water. The pH had changed to 5.25; it was brought back to 6.90 with 0.7 grams of 18% sodium hydroxide.

The suspension was then allowed to settle overnight. Some of the clear supernatant was withdrawn and found to contain 2 ppm aluminum and 10 ppm fluoride.

The suspension was filtered, and the filter cake was washed thoroughly with deionized water, then dried in an oven. Two major (greater than 35 wt. %) crystalline phases were present: $Al(OH)_{1.76}F_{1.24}$ monohydrate and "cryolite". Inductively coupled plasma (ICP) measurement found 11.38 and 11.25 wt. % sodium, and 21.20 and 21.57 wt. % aluminum in duplicate analyses.

Example 6

A slurry of 1450 grams of used aluminum chlorofluoride catalyst containing about 10 wt. % solids was added with stirring to 1450 milliliters of deionized water. The acidic aqueous layer was separated and contained 4.86 wt. % fluoride and 0.88 wt. % chloride. To 300 grams of 23.8 wt. % aqueous calcium chloride solution was added dropwise with stirring 500 grams of this acidic solution of the catalyst. Simultaneously, 992 grams of 6 wt. % sodium hydroxide solution was added dropwise to maintain the pH between 8.2 and 8.9. A precipitate immediately formed. The resultant suspension was stirred overnight and then allowed to settle. The clear supernatant, which had a pH of 8.5, contained 10 ppm dissolved aluminum and less than 5 ppm fluoride.

The precipitate was filtered, washed thoroughly with deionized water and dried in an oven. The major crystalline phase present had an XRD pattern which generally matched that of calcium fluoride. ICP found 14.80 and 15.06 wt. % calcium, and 27.48 and 27.62 wt. % aluminum in duplicate analyses.

Example 7

A slurry of 1990 grams of spent catalyst (about 10% solids) in crude 1,1,1-trichlorotrifluoroethane was added rapidly with stirring to 1900 milliliters of deionized water. The temperature of the mixture rose to about 30° C., and a small amount of organics boiled out of the mixture. The clear, nearly colorless upper aqueous layer was separated from the mixture after it was cooled to about 25° C. This solution of the spent catalyst had a pH of 2.18 and contained 1.57% of aluminum ion.

To 165.17 grams of the solution (0.0958 gram-atom of aluminum ion) was added, with stirring at room temperature, 350 grams of an aqueous solution containing 3.448% of sodium fluoride. This corresponds to an atom ratio of Na/Al of 3.00. The mixture became hazey as solid precipitated. The final pH of the mixture was 2.89. The mixture was allowed to stand at room temperature for one week, and then some of the clear supernate was withdrawn for analyses. It contained 422 ppm of aluminum ion, 919 ppm of fluoride and 1597 ppm of chloride. This corresponds to a 92% removal of the dissolved "$AlF_3$" from the original solution. The solid was collected by filtration, washed with deionized water and oven dried. The X-ray diffraction (XRD) pattern of this solid matched the reference pattern for $Na_3AlF_6$. Inductively coupled plasma (ICP) found 32.3, 32.9% of sodium and 12.0, 12.2% of aluminum in duplicate analyses. The theoretical analysis for $Na_3AlF_6$ is 32.86% of sodium and 12.85% of aluminum.

We claim:

1. A process for treating used aluminum chlorofluoride catalyst comprising mixing the used aluminum chlorofluoride catalyst with water or an aqueous acid to form an aqueous solution, adjusting the pH of the aqueous solution to precipitate and alkali metal aluminum fluoride or an ammonium aluminum fluoride from the aqueous solution, and separating the precipitated alkali metal aluminum fluoride or ammonium aluminum fluoride from the aqueous solution.

2. A process for treating a mixture of used aluminum chlorofluoride catalyst and organics comprising mixing the organics and used aluminum chlorofluoride catalyst with water or an aqueous acid to form an organic phase and an aqueous phase, separating the organic phase from the aqueous phase, adjusting the pH of the aqueous phase to precipitate an alkali metal fluoride or ammonium aluminum fluoride from the aqueous phase, and separating the precipitated alkali metal fluoride or ammonium aluminum fluoride from the aqueous phase.

3. The process of claim 1 or 2 wherein an aqueous alkali is used to adjust the pH.

4. The process of claim 1 or 2 wherein an alkali selected from the group consisting of aqueous sodium hydroxide, aqueous potassium hydroxide and aqueous ammonium hydroxide is used to adjust the pH.

5. The process of claim 2 wherein the organic is 1,1,1-trifluorotrichloroethane.

6. The process of claim 2 wherein the organic is 1,1-difluorotetrachloroethane.

7. The process of claim 2 wherein the organic is 1,1-dichlorotetrafluoroethane.

8. The process of claim 2 wherein the organic is perfluoro-n-pentene-2.

9. The process of claim 2 wherein the organic is a volatile organic, and the process is conducted in a closed system under super-atmospheric pressure to maintain the volatile organic in the liquid phase.

10. A process for treating used aluminum chlorofluoride catalyst comprising mixing the used aluminum chlorofluoride catalyst with water or an aqueous acid to form an aqueous solution, adding a source of calcium with simultaneous or subsequent addition of an alkali to facilitate the precipitation of a calcium fluoride.

* * * * *